United States Patent [19]

Pontoglio et al.

[11] Patent Number: 5,142,090
[45] Date of Patent: Aug. 25, 1992

[54] PROCESS FOR THE PREPARATION OF 3-CYANO-3,5,5'-TRIMETHYL-1-CYCLOHEXANONE

[75] Inventors: Enrico Pontoglio, Brescia; Sandro Parodi, Nuvolento, both of Italy

[73] Assignee: Caffaro S.p.A., Italy

[21] Appl. No.: 585,240

[22] Filed: Sep. 20, 1990

[30] Foreign Application Priority Data

Nov. 2, 1989 [IT] Italy ................................ 22246 A/89

[51] Int. Cl.$^5$ ............................................. C07C 253/10
[52] U.S. Cl. ..................................... 558/341; 558/421
[58] Field of Search ................................. 558/341, 431

[56] References Cited

U.S. PATENT DOCUMENTS 3,352,913 11/1967 Schmitt et al. ................... 558/431 X
4,299,775 11/1981 Dubreux .......................... 558/431 X

FOREIGN PATENT DOCUMENTS 0028179  5/1981  European Pat. Off. ............. 558/341
1047920 11/1966  United Kingdom ................. 558/341

OTHER PUBLICATIONS

Lange, "Manuale Di Chimica", (date not available), pp. 368–369; Uses Utet-Sansoni Edizioni Scientifiche Firenze.

Küster-Thiel, Tabelle Per Le Analisi Chimidre E Chimico-Fisiche, 12th ed, (date not available), p. 138, Ulrico Hoepli Editore Milano.

Primary Examiner—Joseph Paul Brust
Attorney, Agent, or Firm—Wolf, Greenfield & Sacks

[57] ABSTRACT

The present invention relates to a process for the preparation of 3-cyano-3,5,5'-trimethyl-1-cyclohexanone by means of the reaction of isophorone with an alkaline cyanide. The reaction is performed starting from isophorone and an equivalent amount of cyanide in a homogeneous water/organic solvent solution at a temperature comprised between 20° C. and the reflux temperature, maintaining a pH between 14 and 8 by means of a gradual addition of an inorganic acid during the reaction.

20 Claims, No Drawings

PROCESS FOR THE PREPARATION OF 3-CYANO-3,5,5'-TRIMETHYL-1-CYCLOHEXANONE

BACKGROUND OF THE INVENTION

1. Field of the Invention

The present invention relates to a process for the synthesis of [beta]-cyanoketones, in particular 3-cyano-3,5,5'-trimethyl-1-cyclohexanone, starting from isophorone and alkaline cyanides or solutions thereof.

3-cyano-3,5,5'-trimethyl-1-cyclohexanone is the chemical precursor of an important substance, isophorondiamine, which is notoriously used as hardener for epoxy resins and as monomer in the synthesis of polyurethane and polyamide resins.

2. Prior Art

General methods for preparing cyanoketones which provide the 1:4 addition of hydrocyanic acid to the [alpha][beta]-unsaturated ketone are known. The reaction is usually performed in the presence of catalytic amounts of alkaline substances capable of forming cyanide ions. The use of hydrocyanic acid, which is not always easily available, entails problems in handling due to its highly toxic nature.

Therefore, despite the good results which can be achieved with hydrocyanic acid, attempts have nonetheless been made to use directly the more manageable cyanide solutions which however penalize reaction times and yields.

In the European patent application EP 0028179, an attempt has been made to improve the yields of the synthesis by means of a two-phase system. This patent application provides a process in which the organic isophorone solution is placed in contact with the aqueous cyanide solution in the presence of catalytic amounts of a phase transfer agent such as for example quaternary ammonium or phosphonium salts. Yields and reaction times are acceptable, but the amounts of cyanide necessarily used in great excess with respect to the stoichiometric requirement make the process difficult to apply on an industrial scale. This synthesis system, besides being economically negative, in fact creates considerable problems in inertizing the effluents.

It has been so far possible to synthesize 3-cyano-3,5,5'-trimethyl-1-cyclohexanone from isophorone and cyanide in a convenient manner only by resorting to great cyanide excesses.

SUMMARY OF THE INVENTION

A subject of the present invention is a process for the preparation of 3-cyano-3,5,5'-trimethyl-1-cyclohexanone starting from isophorone and stoichiometric amounts of cyanide, so as to be economically more advantageous.

The process is conveniently carried out by performing the reaction of hydrocyaniding isophorone with alkaline cyanide homogeneously in an aqueous-organic solution, simultaneously and gradually feeding appropriate amounts of inorganic acid which are such as to provide, during the reaction, basicity conditions which correspond to measured pH values which decrease continuously as described hereafter.

More particularly, one of the subjects of the present invention is a process for the preparation of 3-cyano-3,5,5'-trimethyl-1-cyclohexanone by means of the reaction of isophorone with an alkaline cyanide, characterized in that the reaction is performed starting from isophorone and equivalent amounts of cyanide, in a homogeneous water/organic solvent solution, at a temperature comprised between 20° C. and the reflux temperature and maintaining a pH between 14 and 8 by means of a gradual addition of an inorganic acid during the reaction.

The organic solvents suitable for the proposed process must be substantially inert, highly polar and miscible with water.

Protophilic solvents, such as methyl or ethyl alcohols, and dipolar aprotic solvents, such as tetrahydrofuran, dioxan, N-methyl-2-pyrrolidone, N,N'dimethylformamide, N,N'dimethylacetamide etc. generally meet these requirements.

Aprotic solvents are particularly preferred due to their limited solvating action with regard to the cyanide anion, which is associated with greater reactivity and a consequently higher reaction rate.

The cyanides which can be used according to the invention are all those which are water-soluble, preferably cyanides of alkaline metals, such as sodium or potassium cyanides. Aqueous solutions of stabilized sodium cyanide, commercially offered at concentrations of approximately 30-35%, can conveniently be used.

The water:solvent weight ratio may vary, also according to the type of organic liquid used, between 0.1:1 and 2:1, preferably between 0.5:1 and 1:1.

One of the characteristics of the process according to the invention is, as mentioned earlier, the gradual feeding, during synthesis, of an acid substance so as to control the pH value, which must decrease continuously from an initial value comprised in the interval between 14 and 11, preferably between 12 and 11, to a reaction end value comprised between 8 and 9, preferably between 8.5 and 9, in a feed time comprised between 1 and 4 hours, preferably between 2 and 3 hours. Once the final pH value has been reached, the reaction is completed in reflux for another 2-3 hours. In the process according to the invention, alkalinity control is performed, as already mentioned, by feeding strong inorganic acids such as phosphoric acid or sulfuric acid. According to the invention, a molar ratio of inorganic acid with respect to the alkaline cyanide which depends on its strength and on its basicity is used; said ratio is kept between 0.8 and 1,2, preferably between 0.95 and 1.05, in the case of a strong monobasic acid; between 0.4 and 0.6, preferably between 0.45 and 0.55, in the case of a strong dibasic acid (e.g. sulfuric acid); between 0.25 and 0.85, preferably between 0.50 and 0.70, in the case of tribasic acid. In particular, however, preference is given to phosphoric acid, both due to its better buffer effect and most of all due to a characteristic consequence of its use.

The Applicant has in fact surprisingly discovered that by working with amounts of phosphoric acid with molar ratios comprised between 0.4 and 0.8, preferably between 0.55 and 0.65, with respect to the alkaline cyanide, it is possible to obtain the neutralization salts in a fluid form.

This circumstance allows to separate the organic phase which contains 3-cyano-3,5,5'-trimethyl-1-cyclohexanone from the saline aqueous phase by simple demixing, without resorting to the more onerous operation of filtration which is unavoidable if other inorganic acids are used.

The temperatures at which the synthesis reaction is performed can range between rather wide limits, comprised between room temperature (20° C.) and the incipient reflux temperature of the solution, but it is usually preferred to operate in the interval comprised between 60° and 120° C., or better still 80°-100° C. Low temperatures in fact extend excessively the hydrocyaniding times, whereas on the contrary high temperatures can privilege secondary reactions (condensation, addition, hydrolysis, etc.).

A further subject of the invention is the elimination of highly toxic effluents the inertizing whereof would entail cost increases and would in any case create further ecological problems related to the disposal of the consequently obtained waste substances.

The process which is a subject of the present invention furthermore has other advantages, such as the possibility of operating with small-size and low-cost plants and of requiring simple industrial technology operations.

Overall reaction times can vary between 1 and 6 hours, preferably between 3 and 4 hours.

A convenient method for performing the process according to the invention, without thereby limiting it in any way, is as follows: isophorone, the chosen organic solvent and the aqueous cyanide solution are initially loaded in the reactor. The load is rapidly heated to the reaction temperature and the feeding, by means of a dosage pump, of the inorganic acid being used is started. The flow rate is adjusted so as to maintain decreasing pH conditions during the reaction.

More conveniently, one operates in a pH interval comprised between 11 and 8.5. Finally, when the reaction is ended, the residual basicity is rapidly acidified until it reaches a slightly acid pH (5-6), and filtration of the part of suspended salts is started. Instead, when phosphoric acid is used, according to the preferred embodiment, as already mentioned, only liquid phases are obtained and the salts are simply eliminated by the demixing operation.

Finally, the solution containing 3-cyano-3,5,5'-trimethyl-1-cyclohexanone is distilled, preferably in two stages.

The water and the solvent are removed in a first stage at atmospheric pressure, or better at a partially reduced pressure; the solvent can recycled to a subsequent synthesis operation, whereas the product is rectified in a second stage at an extremely reduced residual pressure.

The 3-cyano-3,5,5'-trimethyl-1-cyclohexanone yields are in the range of 80% of the theoretical value, but the yields easily reach 90% of the theoretical value by recovering and recycling the unreacted isophorone fraction several times in a preferred embodiment of the process.

A further subject of the present invention is 3-cyano-3,5,5'-trimethyl-1-cyclohexanone obtained according to the above described process.

The following examples are given in order to better illustrate, but not limit, the subject of the invention. The parts (p) are parts by weight unless otherwise specified.

DETAILED DESCRIPTION OF THE PREFERRED EMBODIMENTS

Example 1

553 p of isophorone, 600 p of N,N'dimethylformamide and 600 p of an aqueous solution of 34% sodium cyanide are loaded into a 3000 part by volume reactor equipped with a mechanical agitator, a thermometer, countercurrent coolant and pH measuring probe.

Rapid heating is started so as to raise the temperature to 90°-92° C. and the feeding of 85% $H_3PO_4$ into the reactor is simultaneously started with a flow-rate of approximately 85 p/h.

After two hours, the feeding of the acid is stopped, the temperature is raised to 104°-105° C. and the reaction is allowed to complete for another two hours. The value of the pH measured initially (approximately 11.8) decreases regularly during acidification and stabilizes around 9 when the acid flow is stopped and at 8.5 after the reaction is completed.

Thus, after a total time of four hours, the pH is rapidly brought to 5.5 with a further amount of $H_3PO_4$, thus producing the complete solubilization of the sodium phosphate which had progressively precipitated during the reaction. The total consumption of 85% phosphoric acid is 270 p at the end. By stopping agitation, the reaction mixture demixes without difficulty, forming two liquid phases. The lower layer, with a high density, higher than 1.5, is easily unloaded from the bottom of the reactor at the temperature of 80° C. The upper layer, which contains 3-cyano-3,5,5'-trimethyl-1-cyclohexanone, is then distilled on a Vigreux column with a small number of plates. Water, DMF (dimethylformamide) and low-boiling fractions are removed in a first stage at the absolute pressure of 20-30 mbar and up to the maximum temperature of 100° C. The pressure is reduced further to 1-3 mbar in a second stage and 533 p of crystalline product are collected, in the temperature interval comprised between 100° and 120° C., after a first liquid fraction of approximately 50 p mainly constituted by isophorone and 3-cyano-3,5,5'-trimethyl-1-cyclohexanone. IR and HPLC analyses confirm that it is 97% 3-cyano-3,5,5'-trimethyl-1-cyclohexanone, which corresponds to a yield of 78%.

Example 2

Synthesis is repeated with the same methods used for example 1, but the nature of the initial load is modified. In this case, approximately 85% of the DMF is replaced with a recycling mixture which derives from the preparation of the previous example and is constituted by distilled DMF and by the fraction of the second rectification stage. In particular, 450 g of DMF and 50 g of liquid fraction are recycled.

After the conventional distillation operations, 52 g of liquid fraction and 611 g of crystalline product are again obtained.

HPLC analysis again confirms a titer of 98%.

The example therefore demonstrates that the overall yield, in recycling conditions, is easily raised to 90%.

We claim:

1. A process for the preparation of 3-cyano-3,5,5'-trimethyl-1-cyclohexanone by means of a reaction of isophorone with an alkaline cyanide, wherein the reaction is performed starting from isophorone and said alkaline cyanide in a homogeneous water/organic solvent solution at a temperature between about 20° C. and a reflux temperature of the solution and maintaining a pH between about 14 and 8 by means of gradual addition of phosphoric acid during the reaction in an acid:cyanide molar ratio of between about 0.4 and 0.8, said acid sufficient to obtain in fluid form neutralization salts produced by the reaction of said phosphoric acid with said alkaline cyanide.

2. Process according to claim 1, wherein the pH value decreases from an initial value between about 14 and 11 to a reaction end value between about 8 to 9.

3. Process according to claim 1, wherein the inorganic acid addition time is between about 1 to 4 hours.

4. Process according to claim 3, wherein the inorganic acid addition time is between about 2 and 3 hours.

5. Process according to claim 1, wherein the reaction is performed at a temperature between about 60° C. and 120° C.

6. Process according to claim 5, wherein the reaction is performed at a temperature between about 80° C. and 100° C.

7. Process according to claim 1, wherein after reaching the final pH the reaction solution is kept at the reflux temperature for another 2–3 hours.

8. Process according to claim 1, wherein the organic solvent is highly polar and substantially inert to the components present during the reaction.

9. Process according to claim 8, wherein the organic solvent is at least one solvent selected from the group consisting of methyl alcohol, ethyl alcohol, tetrahydrofuran, dioxan, N-methyl-2-pyrrolidone, N,N-dimethylformamide and N,N'-dimethylacetamide.

10. Process according to claim 1, wherein said water:organic solvent weight ratio is between about 0.1:1 and 2:1.

11. Process according to claim 10, wherein said water:organic solvent weight ratio is between about 0.5:1 and 1:1.

12. Process according to claim 1, wherein an inorganic acid/alkaline cyanide molar ratio of between about 0.25 to 1.2 is used.

13. Process according to claim 1, wherein, the phosphoric acid:alkaline cyanide molar ratio is between about 0.55 and 0.65.

14. Process according to claim 1, wherein when the reaction is completed the residual basicity is rapidly acidified until a pH value of 5–6 is reached and the suspended salts are separated by filtration.

15. Process according to claim 1, wherein said reflux temperature is maintained over a time period on the order of 3–7 hours.

16. The process of claim 1, further comprising forming, upon addition of said inorganic acid, a two-phase solution comprising an aqueous saline layer including said solubilized neutralization salts and an organic layer comprising 3-cyano-3,5,5'-trimethyl-1-cyclohexanone;

separating said aqueous saline layer from said organic layer; and separating 3-cyano-3,5,5'-trimethyl-1-cyclohexanone from said organic layer.

17. A process for preparation of 3-cyano-3,5,5'-trimethyl-1-cyclohexanone comprising the steps of:

(a) forming a reaction mixture of isophorone with an alkaline cyanide in the presence of an organic solvent, said reaction mixture formed as a single phase water/solvent solution;

(b) refluxing said reaction mixture at a temperature of at least 20° C.;

(c) providing a gradually decreasing pH in said reaction mixture by gradual addition to said mixture of an inorganic acid selected from the group consisting of sulfuric acid and phosphoric acid;

(d) separating an organic fraction containing 3-cyano-3,5,5'-trimethyl-1-cyclohexanone from said reaction mixture;

(e) separating the organic solvent from said organic fraction of step (d); and (f) returning a portion of the separated organic solvent to the reaction mixture of step (a).

18. The process of claim 17, wherein the organic solvent is selected from the group consisting of methyl alcohol, ethyl alcohol, tetrahydrofuran, dioxan, N-methyl-2-pyrrolidone, N,N-dimethylformamide and N,N'-dimethylacetamide.

19. A process for preparing 3-cyano-3,5,5'-trimethyl-1-cyclohexanone, comprising:

combining isophorone and an alkaline cyanide in an organic solvent to form a reaction mixture; heating the reaction mixture to a temperature between about 80° C. to 100° C.; adding phosphoric acid to the reaction mixture to yield an acid:cyanide molar ratio of between about 0.55 and 0.65;

adding increasing amounts of phosphoric acid to decrease acidity of the mixture to about 8.5;

further acidifying the mixture to a pH of between about 5–6 by addition of phosphoric acid to produce complete solubilization of neutralization salts formed during the reaction; separating said solubilized salts from said reaction mixture; and distilling from the reaction mixture an organic fraction containing 3-cyano-3,5,5'-trimethyl-1-cyclohexanone to remove organic solvent.

20. The process of claim 16, further comprising separating the organic solvent from said organic layer and returning a portion of the separated organic solvent to the water/organic solvent solution.

* * * * *